US009245518B2

(12) United States Patent
Sakamoto et al.

(10) Patent No.: US 9,245,518 B2
(45) Date of Patent: Jan. 26, 2016

(54) ACTIVE VIBRATION NOISE CONTROL APPARATUS

(75) Inventors: Kosuke Sakamoto, Utsunomiya (JP); Toshio Inoue, Tochigi-ken (JP)

(73) Assignee: Honda Motor Co., Ltd., Tokyo (JP)

( * ) Notice: Subject to any disclaimer, the term of this patent is extended or adjusted under 35 U.S.C. 154(b) by 608 days.

(21) Appl. No.: 13/354,068

(22) Filed: Jan. 19, 2012

(65) Prior Publication Data

US 2012/0189132 A1 Jul. 26, 2012

(30) Foreign Application Priority Data

Jan. 21, 2011 (JP) ................................ 2011-010334

(51) Int. Cl.

| | |
|---|---|
| ***A61F 11/06*** | (2006.01) |
| ***G10K 11/16*** | (2006.01) |
| ***H03B 29/00*** | (2006.01) |
| ***G10K 11/178*** | (2006.01) |

(52) U.S. Cl.

CPC .......... *G10K 11/178* (2013.01); *G10K 11/1786* (2013.01); *G10K 11/1788* (2013.01); *G10K 2210/12821* (2013.01); *G10K 2210/3023* (2013.01)

(58) Field of Classification Search

CPC .............. G10K 11/175; G10K 11/178; G10K 11/1782; G10K 11/1784; G10K 11/1786; G10K 11/1788; G10K 2210/128; G10K 2210/1282; G10K 2210/12821; G10K 2210/129; G10K 2210/1291; H04R 2499/13

USPC ......... 381/71.1, 71.2, 71.4, 71.6, 71.11, 73.1, 381/86; 701/10, 387, 37–40; 280/5.5

See application file for complete search history.

(56) References Cited

U.S. PATENT DOCUMENTS

| | | | | |
|---|---|---|---|---|
| 5,701,349 | A | 12/1997 | Sano et al. | |
| 5,794,168 | A * | 8/1998 | Sasaki et al. | 701/37 |
| 2004/0247137 | A1 | 12/2004 | Inoue et al. | |
| 2007/0179679 | A1* | 8/2007 | Flament et al. | 701/1 |
| 2008/0249689 | A1* | 10/2008 | Matsumoto et al. | 701/48 |
| 2011/0142248 | A1 | 6/2011 | Sakamoto et al. | |
| 2013/0259249 | A1* | 10/2013 | Sakamoto et al. | 381/71.4 |

FOREIGN PATENT DOCUMENTS

| | | | |
|---|---|---|---|
| EP | 2 329 993 | A1 | 6/2011 |
| JP | 06-203491 | A | 7/1964 |
| JP | 03-203491 | A | 9/1991 |
| JP | 06-083369 | A | 3/1994 |
| JP | 06-110473 | A | 4/1994 |

(Continued)

OTHER PUBLICATIONS

Japanese Office Action, Japanese Application No. 2011-010334, dated Aug. 13, 2013.

(Continued)

*Primary Examiner* — Xu Mei

(74) *Attorney, Agent, or Firm* — Carrier Blackman & Associates, P.C.; William D. Blackman; Joseph P. Carrier

(57) ABSTRACT

An active vibration noise control apparatus uses an adaptive control process, which predicts rear road wheel noise canceling sounds by correcting a front road wheel reference signal or a rear road wheel reference signal with a corrective filter, based on different characteristics of front road wheel suspensions and rear road wheel suspensions.

8 Claims, 10 Drawing Sheets

(56) References Cited

FOREIGN PATENT DOCUMENTS

| | | | | |
|---|---|---|---|---|
| JP | 06-203491 | A | | 7/1994 |
| JP | 07-210179 | A | | 8/1995 |
| JP | 08-216642 | A | | 8/1996 |
| JP | 2007-216787 | A | | 8/2007 |
| JP | 2007216787 | A | * | 8/2007 |
| WO | WO 2010/032517 | A1 | | 3/2010 |

OTHER PUBLICATIONS

Chinese Office Action, Chinese Application No. 201210012873.5, dated Jan. 6, 2014.

Notice of Allowance, dated Sep. 30, 2014, issued over the corresponding JP Patent Application No. 2011-010334 with the English translation of the pertinent portion.

* cited by examiner

ACTIVE VIBRATION NOISE CONTROL APPARATUS

CROSS-REFERENCE TO RELATED APPLICATION

This application is based upon and claims the benefit of priority from Japanese Patent Application No. 2011-010334 filed on Jan. 21, 2011, of which the contents are incorporated herein by reference.

BACKGROUND OF THE INVENTION

1. Field of the Invention

The present invention relates to an active vibration noise control apparatus for canceling vibration noise based on an input from a road surface with canceling sounds, and more particularly to an active vibration noise control apparatus for canceling vibration road noise according to an adaptive control process.

2. Description of the Related Art

Active noise control apparatus (hereinafter referred to as "ANC apparatus") are known in the art as apparatus for controlling acoustics in relation to vibration noise in vehicular passenger compartments. According to a general ANC apparatus, speakers in a vehicular passenger compartment output canceling sounds in opposite phase with the vibration noise to reduce the vibration noise in the vehicular passenger compartment. An error representing a deviation between the vibration noise and the canceling sounds is detected as residual noise by a microphone, which is positioned near the ears of a passenger in the vehicular passenger compartment, and is used to determine the canceling sounds. Some ANC apparatus reduce noise (muffled engine sounds), which is generated in the vehicular passenger compartment as the engine operates (vibrates). See, for example, U.S. Patent Application Publication No. 2004/0247137 (hereinafter referred to as "US 2004/0247137 A1"), Japanese Laid-Open Patent Publication No. 06-083369 (hereinafter referred to as "JP 06-083369 A"), and Japanese Laid-Open Patent Publication No. 2007-216787 (hereinafter referred to as "JP 2007-216787 A")}.

According to JP 06-083369 A, vibrations of front road wheels are detected by a pickup (1) located near the front road wheels. Canceling sounds for canceling vibration noise caused by vibrations of the front road wheels are generated based on an output signal (reference signal) from the pickup (1). The output signal (reference signal) from the pickup (1) is delayed by a delay circuit (4) depending on vehicle speed. Canceling sounds for canceling vibration noise caused by vibrations of the rear road wheels is generated based on the delayed reference signal (see, for example, Abstract, FIG. 1, and paragraphs [0018] through [0026]).

According to JP 2007-216787 A, vibrations applied from the front road wheels to the vehicle body are detected by acceleration sensors (14, 16) located near the front road wheels. Vibrations applied from the rear road wheels to the vehicle body are estimated based on detected signals from the acceleration sensors (14, 16) and a vehicle speed sensor (26). Canceling sounds are generated and output based on estimated vibrations applied from the rear road wheels to the vehicle body and vibration noise detected by a microphone (30) (see, for example, Abstract and FIG. 1).

SUMMARY OF THE INVENTION

According to JP 06-083369 A and JP 2007-216787 A, as described above, vibrations of the rear road wheels are estimated based on vibrations of the front road wheels and vehicle speed, and canceling sounds for both vibration noise from the front road wheels and vibration noise from the rear road wheels are generated. Stated otherwise, it is assumed that vibrations of the rear road wheels, which are identical to the vibrations of the front road wheels, are produced with a certain time delay from the vibrations of the front road wheels.

However, vehicles may not necessarily have front road wheel suspensions and rear road wheel suspensions that are identical to each other. For example, the front road wheels are combined with a steering mechanism for changing the direction of the vehicle, whereas the rear road wheels normally are not combined with such a steering mechanism. Front-wheel-drive vehicles include a drive shaft connected to the front road wheels with no drive shaft connected to the rear road wheels. Some vehicles also include a subframe associated with the front road wheels with no subframe associated with the rear road wheels. Further, if vehicles have different weights on the front road wheels and the rear road wheels, respectively, then the front and rear road wheel suspensions require different spring characteristics and damping characteristics. Consequently, estimating vibrations of the rear road wheels simply by delaying the vibrations of the front road wheels may not be capable of outputting accurate canceling sounds responsive to the vibration noise from the rear road wheels.

It is an object of the present invention to provide an active vibration noise control apparatus with an increased noise silencing capability.

According to the present invention, there is provided an active vibration noise control apparatus comprising a front road wheel vibration detecting unit for detecting front road wheel vibrations based on an input applied from a road surface to a front road wheel of a vehicle, and outputting a front road wheel reference signal representative of the detected front road wheel vibrations, a vehicle speed detecting unit for detecting a vehicle speed of the vehicle, a delay time calculating unit for determining a delay time which is representative of the difference between respective times when the front road wheel of the vehicle and a rear road wheel of the vehicle pass through a point, based on the vehicle speed, a rear road wheel reference signal outputting unit for outputting a rear road wheel reference signal, which is representative of predicted rear road wheel vibrations, comprising the front road wheel vibrations delayed by the delay time, and a canceling sound outputting unit for outputting a front road wheel noise canceling sound which cancels out front road wheel vibration noise caused by the front road wheel vibrations at a noise silencing position, based on the front road wheel reference signal, and outputting a rear road wheel noise canceling sound which cancels out rear road wheel vibration noise caused by the predicted rear road wheel vibrations at the noise silencing position, based on the rear road wheel reference signal, wherein the rear road wheel reference signal outputting unit predicts the rear road wheel noise canceling sound by correcting the front road wheel reference signal or the rear road wheel reference signal with a corrective filter, based on different characteristics of front road wheel suspensions and rear road wheel suspensions of the vehicle.

With the above arrangement, it is possible to predict the rear road wheel noise canceling sound nicely from the front road wheel reference signal in view of the different characteristics of the front road wheel suspensions and the rear road wheel suspensions.

The rear road wheel reference signal outputting unit may change characteristics of the corrective filter depending on an amplitude of the front road wheel reference signal. When the amplitude of the front road wheel reference signal is changed, the spring characteristics of the front road wheel suspensions, for example, are changed. With the above arrangement, characteristics of the corrective filter are changed depending on the amplitude of the front road wheel reference signal. Therefore, it is possible to output the rear road wheel noise canceling sound depending on respective spring characteristics of the front road wheel suspensions and the rear road wheel suspensions, thereby increasing the accuracy with which the rear road wheel noise canceling sound is predicted.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
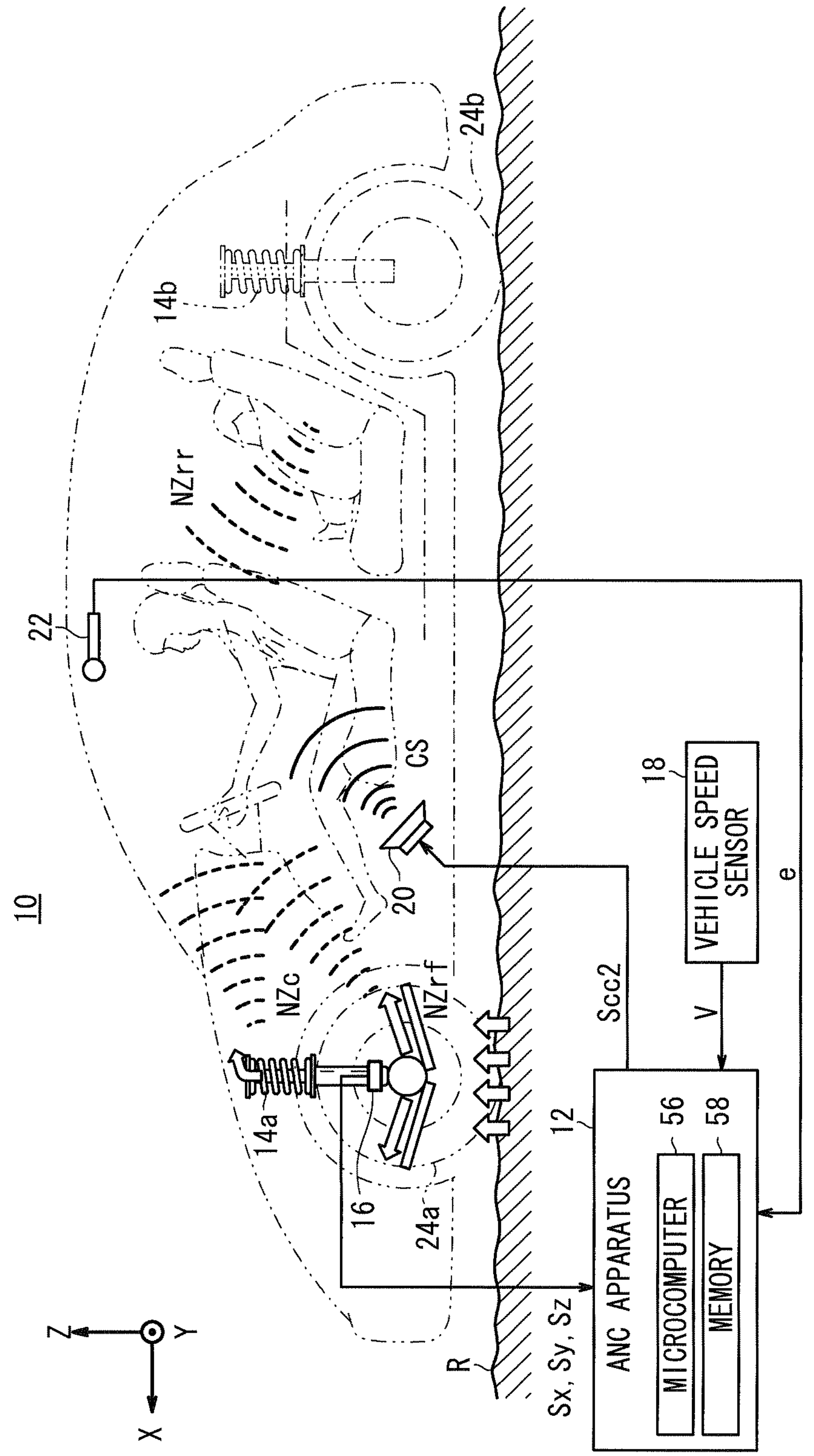
FIG. 1 is a schematic view of a vehicle incorporating an active vibration noise control apparatus according to an embodiment of the present invention.

Like or corresponding parts are denoted by like or corresponding reference characters throughout the views.

A. Embodiment

1. Overall and Partial Configurations (1) Overall Configuration

FIG. 1 is a schematic view of a vehicle 10 incorporating an active vibration noise control apparatus 12 (hereinafter referred to as "ANC apparatus 12") according to an embodiment of the present invention. The vehicle 10 may be a gasoline-powered vehicle, an electric vehicle (including a fuel cell vehicle), or the like.

The vehicle 10 includes, in addition to the ANC apparatus 12, a plurality of front road wheel suspensions 14*a*, a plurality of rear road wheel suspensions 14*b*, a plurality of acceleration sensor units 16 associated respectively with the front road wheel suspensions 14*a*, a vehicle speed sensor (vehicle speed detecting unit) 18 for detecting a vehicle speed V [km/h] of the vehicle 10, a speaker (canceling sound outputting unit) 20, and a microphone 22.

The ANC apparatus 12 generates a second combined control signal Scc2 based on acceleration signals Sx, Sy, Sz from the acceleration sensor units 16, a vehicle speed V detected by the vehicle speed sensor 18, and an error signal e from the microphone 22. The second combined control signal Scc2 is amplified by an amplifier (not shown) and then is supplied to the speaker 20. The speaker 20 outputs a canceling sound CS corresponding to the second combined control signal Scc2.

Figure 2:
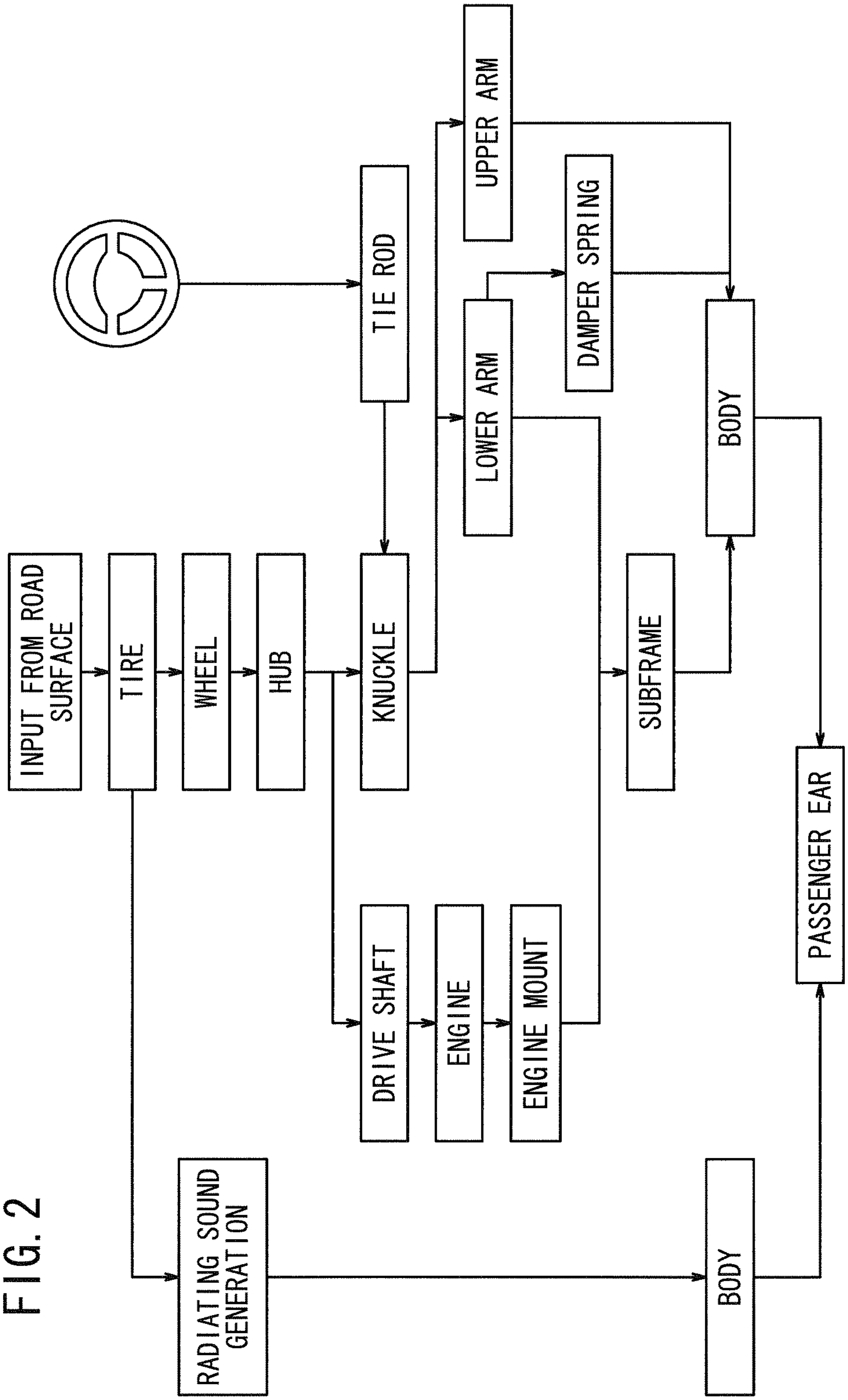
FIG. 2 is a block diagram showing paths along which road noise applied to road wheels is transmitted to ears of a passenger in the vehicle.

Vibration noise generated in the passenger compartment of the vehicle 10 is constituted by composite vibration noise NZc, which is made up of vibration noise (muffled engine sounds NZe) produced when the engine (not shown) of the vehicle vibrates, and vibration noise (road noise NZr) produced as the road wheels (left and right front road wheels 24*a* and left and right rear road wheels 24*b*) travel in contact with a road surface R and vibrate. The ANC apparatus 12 according to the present embodiment produces a sound silencing effect for canceling road noise NZr made up the composite vibration noise NZc with the canceling sound CS. The road noise NZr includes noises due to vibrations applied from the left and right front road wheels 24*a* (front road wheel road noise NZrf), and noises due to vibrations applied from the left and right rear road wheels 24*b* (rear road wheel road noise NZrr). The road noise applied from the road surface R to the road wheels 24 is transmitted to the ears of a passenger along the paths as shown in FIG. 2, for example.

The ANC apparatus 12 may also include a sound silencing function for silencing muffled engine sounds NZe, in addition to the sound silencing function for silencing road noise NZr. In other words, the ANC apparatus 12 may incorporate a conventional system for silencing muffled engine sounds (see, for example, US 2004/0247137 A1).

Figure 4:
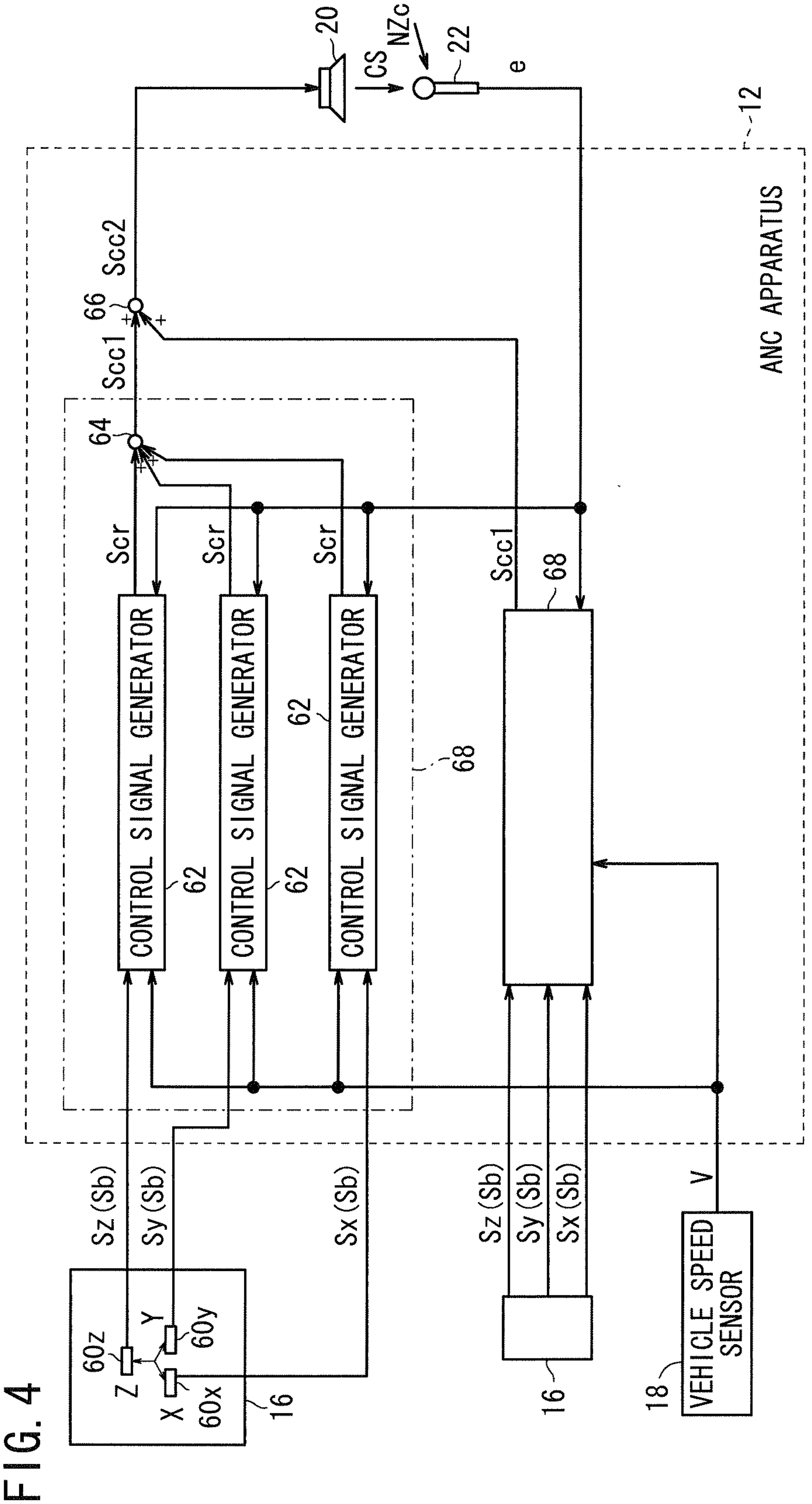
FIG. 4 is a functional block diagram of the active vibration noise control apparatus.
Figure 5:
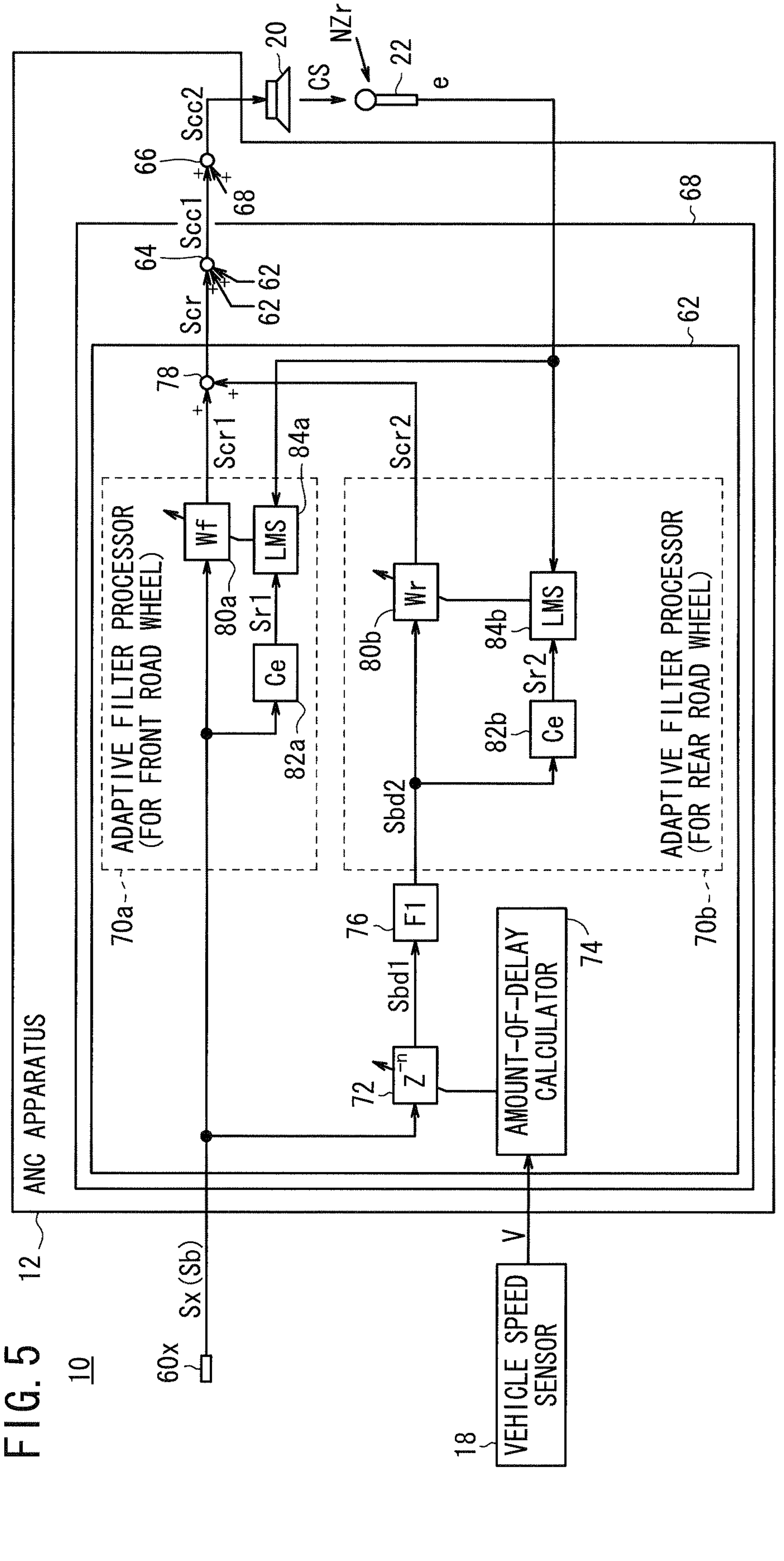
FIG. 5 is a functional block diagram of a control signal generator of the active vibration noise control apparatus.

Although not shown in FIG. 1, the acceleration sensor units 16 are associated respectively with the left and right front road wheels 24*a* (see FIG. 4). In FIGS. 1, 4 and 5, the speaker 20 and the microphone 22 are illustrated as one speaker and one microphone, respectively. However, depending on how the ANC apparatus 12 is applied, the vehicle 10 may have a plurality of speakers and a plurality of microphones. If the vehicle 10 has a plurality of speakers and a plurality of microphones, then the ANC apparatus 12 further includes a plurality of corresponding components, which are associated respectively with the plurality of speakers and microphones.

(2) Front Road Wheel Suspensions 14*a* and Acceleration Sensor Units 16

Figure 3:
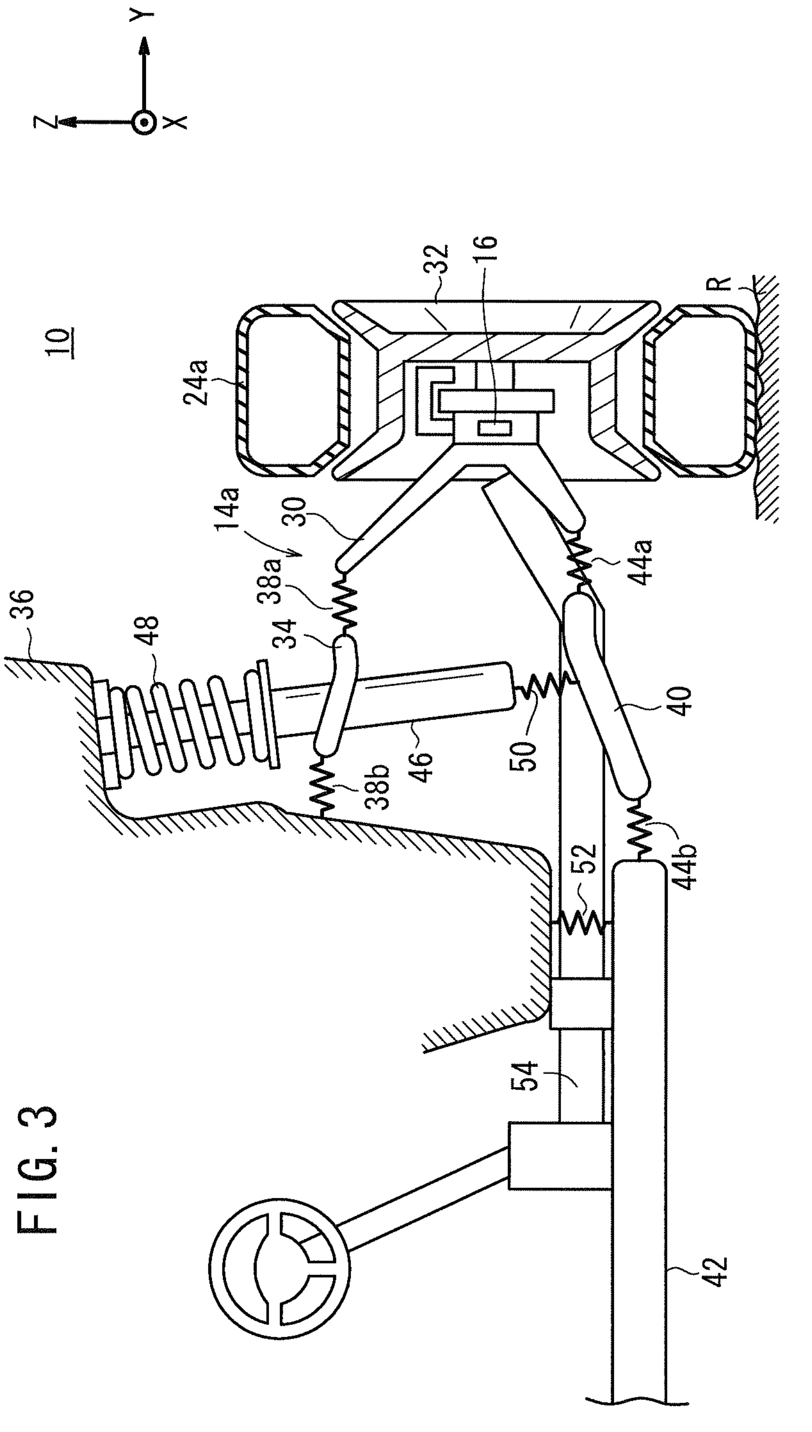
FIG. 3 is a cross-sectional view showing an acceleration sensor and nearby parts mounted on the vehicle.

As shown in FIG. 3, each of the acceleration sensor units 16 is mounted on a knuckle 30 coupled to a wheel 32 of the front road wheel 24*a*, which is supported by one of the front road wheel suspensions 14*a*. The front road wheel suspension 14*a* includes, in addition to the knuckle 30, an upper arm 34 connected to the knuckle 30 and a vehicle body 36 by respective joints 38*a*, 38*b*, a lower arm 40 connected to the knuckle 30 and a vehicle subframe 42 by respective joints 44*a*, 44*b*, and a damper 46 connected to the vehicle body 36 by a damper spring 48 and to the lower arm 40 by a joint 50. The vehicle body 36 and the vehicle subframe 42 are connected to each other by a joint 52. A drive shaft 54 is rotatably inserted in the knuckle 30.

As shown in FIG. 4, each of the acceleration sensor units 16 includes an acceleration sensor (front road wheel vibration detecting unit) 60*x* for detecting a vibrational acceleration Ax, an acceleration sensor (front road wheel vibration detecting unit) 60*y* for detecting a vibrational acceleration Ay, and an acceleration sensor (front road wheel vibration detecting unit) 60*z* for detecting a vibrational acceleration Az. The vibrational acceleration Ax, which is detected by the acceleration sensor 60*x*, represents a vibrational acceleration [mm/s/s] of the knuckle 30 along longitudinal directions (X-axis directions in FIG. 1) of the vehicle 10. The vibrational acceleration Ay, which is detected by the acceleration sensor 60*y*, represents a vibrational acceleration [mm/s/s] of the knuckle 30 along transverse directions (Y-axis directions in FIG. 3) of the vehicle 10. The vibrational acceleration Az, which is detected by the acceleration sensor 60*z*, represents a vibrational acceleration [mm/s/s] of the knuckle 30 along vertical directions (Z-axis directions in FIG. 1) of the vehicle 10.

Each of the acceleration sensor units 16 outputs to the ANC apparatus 12 acceleration signals Sx, Sy, Sz, which are indicative of the vibrational accelerations Ax, Ay, Az detected at the knuckle 30. The ANC apparatus 12 generates the canceling sound CS using the acceleration signals Sx, Sy, Sz, which have been converted from an analog form into a digital form, as reference signals Sb. The acceleration signals Sx, Sy, Sz will hereinafter also be referred to as reference signals Sb.

(3) ANC Apparatus 12

(a) Overall Configuration

The ANC apparatus 12 serves to control the output of the canceling sound CS from the speaker 20, and includes a microcomputer 56, a memory 58 (see FIG. 1), etc. The microcomputer 56 performs functions including a function to determine the canceling sound (canceling sound determining function) according to software processing.

FIG. 4 is a functional block diagram of the ANC apparatus 12. As shown in FIG. 4, the ANC apparatus 12 includes a plurality of control signal generators 62 associated respectively with the acceleration sensors 60*x*, 60*y*, 60*z*, a first adder 64 provided in association with each of the acceleration sensor units 16 of the front road wheels 24*a*, and a second adder 66 provided in association with each of the acceleration sensor units 16 of the front road wheels 24*a*. The control signal generators 62, the first adder 64, and the second adder 66 are implemented by software via the microcomputer 56 and the memory 58.

In the present embodiment, the acceleration signals Sx, Sy, Sz output from the acceleration sensor units 16 are analog signals, which are converted by analog-to-digital converters (not shown) in the ANC apparatus 12 into digital acceleration signals Sx, Sy, Sz that are applied to the respective control signal generators 62. The second combined control signal Scc2, which is output as a digital signal from the second adder 66, is converted by a digital-to-analog converter (not shown) in the ANC apparatus 12 into an analog second combined control signal Scc2 that is applied to the speaker 20.

For illustrative purposes, the control signal generators 62 and the first adder 64, which are associated respectively with each of the acceleration sensor units 16, will be referred to collectively as a control signal generating unit 68. In FIG. 4, the ANC apparatus 12 is shown as including two upper and lower control signal generating units 68, with the upper control signal generating unit 68 having internal details as illustrated, and the lower control signal generating unit 68 having internal details, which are omitted from illustration.

(b) Control Signal Generator 62

FIG. 5 is a functional block diagram of one of the control signal generators 62. FIG. 5 shows the control signal generator 62, which is associated with the acceleration sensor 60*x*. The other control signal generators 62, which are associated respectively with the acceleration sensors 60*y* and 60*z*, are identical in configuration to the control signal generator 62 shown in FIG. 5.

As shown in FIG. 5, the control signal generator 62 includes a pair of adaptive filter processors (canceling sound outputting unit) 70*a*, 70*b*, a delay setting section (rear road wheel reference signal outputting unit) 72, an amount-of-delay calculator (delay time calculating unit) 74, a corrective filter 76, and an adder 78.

The adaptive filter processor 70*a* is associated with vibrations (measured value) applied from the front road wheel 24*a*. The adaptive filter processor 70*a* performs an adaptive filter control process on the acceleration signal Sx (reference signal Sb), which has been converted into a digital signal. The adaptive filter processor 70*a* includes an adaptive filter 80*a*, a reference signal corrector 82*a*, and a filter coefficient updater 84*a*.

The adaptive filter 80*a* comprises an FIR (Finite Impulse Response) filter or an adaptive notch filter, for example. The adaptive filter 80*a* performs an adaptive filter process on the reference signal Sb using a filter coefficient Wf, and outputs a front road wheel control signal Scr1, which represents a waveform of a canceling sound CS (front road wheel noise canceling sound CSf) for reducing the front road wheel road noise NZrf corresponding to the road vibrations (measured value) applied from the front road wheel 24*a*.

The reference signal corrector 82*a* generates a corrective reference signal Sr1 by performing a transfer function process on the reference signal Sb. The corrective reference signal Sr1 is used by the filter coefficient updater 84*a* when the filter coefficient updater 84*a* calculates a filter coefficient Wf. The transfer function process is a process for correcting the reference signal Sb based on a transfer function Ce (filter coefficient) of the canceling sound CS from the speaker 20 and the microphone 22. The transfer function Ce, which is used in the transfer function process, represents a measured value or a predicted value of the actual transfer function C of the canceling sound CS from the speaker 20 to the microphone 22.

The filter coefficient updater 84*a* sequentially calculates and updates the filter coefficient Wf. The filter coefficient updater 84*a* calculates and updates the filter coefficient Wf according to an adaptive algorithm, e.g., a least-mean-square (LMS) algorithm. More specifically, the filter coefficient updater 84*a* calculates the filter coefficient Wf so as to eliminate the square $e^2$ of the error signal e, based on the corrective reference signal Sr1 from the reference signal corrector 82*a* and the error signal e from the microphone 22. A specific calculating process used by the filter coefficient updater 84*a* may, for example, be the process disclosed in US 2004/0247137 A1.

The delay setting section 72 outputs a first delayed reference signal Sbd1, which is produced by imparting to the reference signal Sb a delay having a delay amount n calculated by the amount-of-delay calculator 74.

The amount-of-delay calculator 74 calculates a delay amount n, which is used by the delay setting section 72. More specifically, the amount-of-delay calculator 74 calculates the delay amount n according to the following equation (1):

$$n=[Lwb/\{V\times1000/(60\times60)\}]/Pc \quad (1)$$

(rounded down to the nearest whole number)

In equation (1), Lwb represents the wheelbase [m] of the vehicle 10, i.e., the distance between the axle of the front road wheels 24*a* and the axle of the rear road wheels 24*b*, V represents the vehicle speed [km/h] from the vehicle speed sensor 18, and Pc represents a calculating period [sec]. The number "1000/(60×60)" in equation (1) represents a coefficient for converting the vehicle speed V from kilometers per hour into meters per second [m/sec]. If the vehicle speed V is defined in meters per second from the outset, then such a coefficient becomes unnecessary. The delay amount n calculated according to equation (1) may be rounded up or rounded off, rather than being rounded down.

As can be seen from equation (1), the delay amount n according to the present embodiment represents an amount by which the reference signal Sb (the first delayed reference signal Sbd1) for the rear road wheels 24*b* is delayed from the calculating period Pc of the reference signal Sb for the front road wheels 24*a*. In the present embodiment, only the vehicle speed V is variable in equation (1). Therefore, instead of performing the calculation of equation (1), a map, which defines the relationship between vehicle speeds V and delay quantities n, may be stored in the memory 58, and the delay amount n may be selected from the map depending on the present vehicle speed V.

The corrective filter 76 comprises an FIR filter or an IIR (Infinite Impulse Response) filter. The corrective filter 76 performs a process on the first delayed reference signal Sbd1 depending on a preset transfer function F1, and outputs a second delayed reference signal Sbd2. More specifically, the corrective filter 76 presets a transfer function F1 in the following manner.

Figure 6:
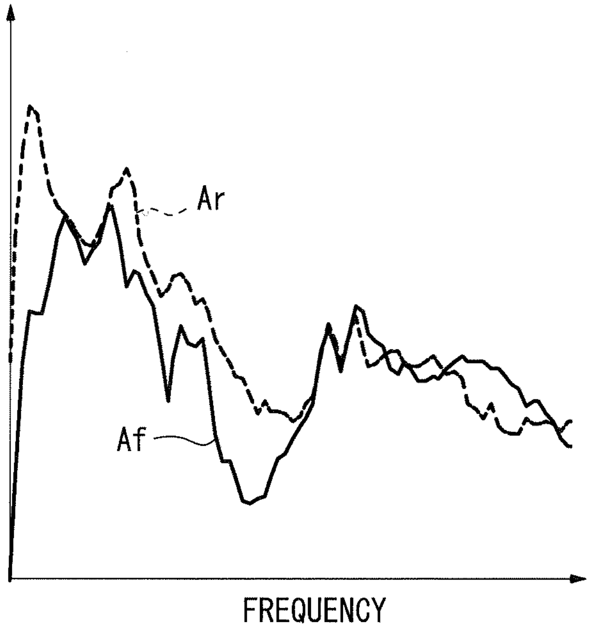
FIG. 6 is a diagram showing by way of example a relationship between frequencies and amplitudes of vibrations of front road wheels and rear road wheels.
Figure 7:
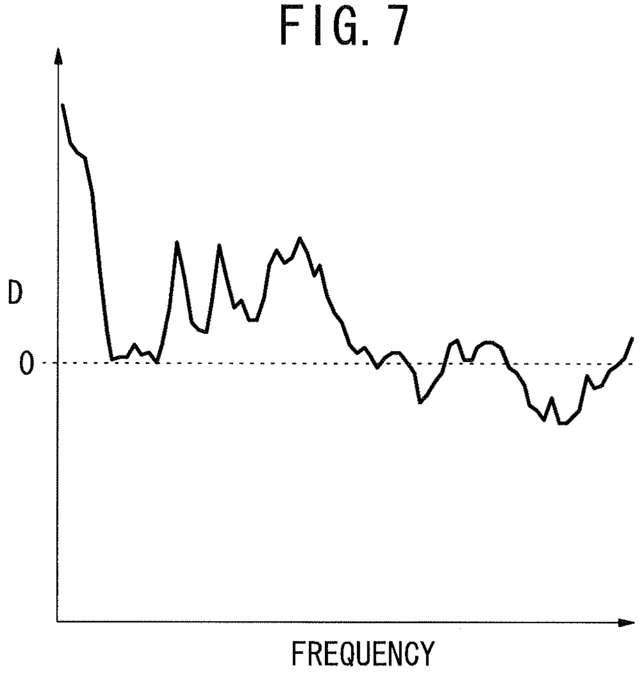
FIG. 7 is a diagram showing by way of example a relationship between frequencies of vibrations of front road wheels and rear road wheels and the difference between amplitudes of the vibrations.

Before the vehicle 10 is shipped out of the factory, an acceleration sensor unit 16 is installed on each of the rear road wheel suspensions 14*b*. Then, output signals are produced from the acceleration sensor units 16 installed on the front road wheel suspensions 14*a* and the rear road wheel suspensions 14*b*. FIG. 6 shows by way of example the relationship between frequencies and amplitudes Af, Ar of the acceleration signals Sx, from acceleration sensors 60*x* mounted on the front road wheel suspensions 14*a* and the rear road wheel suspensions 14*b*. Data (amplitude Ar) from the rear road wheels 24*b* was acquired at a given time, which was delayed by the delay amount n from the time at which data (amplitude Af) was acquired from the front road wheels 24*a*. FIG. 7 shows deviations D between the amplitude Af and the amplitude Ar at each frequency.

According to the present embodiment, the deviations D shown in FIG. 7 are determined as measured values, and the transfer function F1 (in particular, the gain) of the corrective filter 76 is established in order to correct the deviations D, from among such deviations, at frequencies or within a frequency range where road noise NZr tends to occur.

As described above, the delay amount n is determined from the wheelbase Lwb of the vehicle 10, the vehicle speed V, and the calculating period Pc. The difference between times, over which the front road wheel noise canceling sound CSf and the rear road wheel noise canceling sound CSr reach the ears of the passenger, changes due to other factors (e.g., distances from the speakers to the ears of the passenger, if there are a plurality of vibration paths and a plurality of speakers). Therefore, the corrective filter 76 can adjust the phase to reflect not only the gain, but also differences between such times.

The adaptive filter processor 70*b* of FIG. 5 is associated with vibrations (estimated value) applied from the rear road wheel 24*b*, and is identical in configuration to the adaptive filter processor 70*a*. However, instead of the reference signal Sb, the adaptive filter processor 70*b* uses the second delayed reference signal Sbd2. Therefore, a rear road wheel control signal Scr2, which is output from the adaptive filter 80*b* of the adaptive filter processor 70*b*, represents the waveform of the rear road wheel noise canceling sound CSr for reading the rear road wheel road noise NZrr, which corresponds to road surface vibrations (estimated value) applied from the rear road wheels 24*b*.

The third adder 78 combines the front road wheel control signal Scr1 from the adaptive filter processor 70*a* and the rear road wheel control signal Scr2 from the adaptive filter processor 70*b* into a control signal Scr.

(c) First Adder 64

The first adder 64 combines control signals Scr output from the respective control signal generators 62 into a first combined control signal Scc1.

(d) Second Adder 66

The second adder 66 combines the first combined control signals Scc1 output from the first adders 64 of the respective control signal generators 62 into a second combined control signal Scc2. The second combined control signal Scc2 is converted by a digital-to-analog converter (not shown) in the ANC apparatus 12 into an analog second combined control signal Scc2, which is applied to the speaker 20.

(4) Speaker 20

The speaker 20 outputs a canceling sound CS corresponding to the second combined control signal Scc2 from the ANC apparatus 12 (microcomputer 56), thereby providing a sound silencing effect in order to silence road noise NZr, which represents the sum of the front road wheel road noise NZrf and the rear road wheel road noise NZrr.

(5) Microphone 22

The microphone 22 detects an error representing the difference between the road noise NZr and the canceling sound CS as residual noise, and outputs an error signal e indicative of such residual noise to the ANC apparatus 12 (microcomputer 56).

2. Processing Sequence of Various Components (for Generating Canceling Sounds CS)

Figure 8:
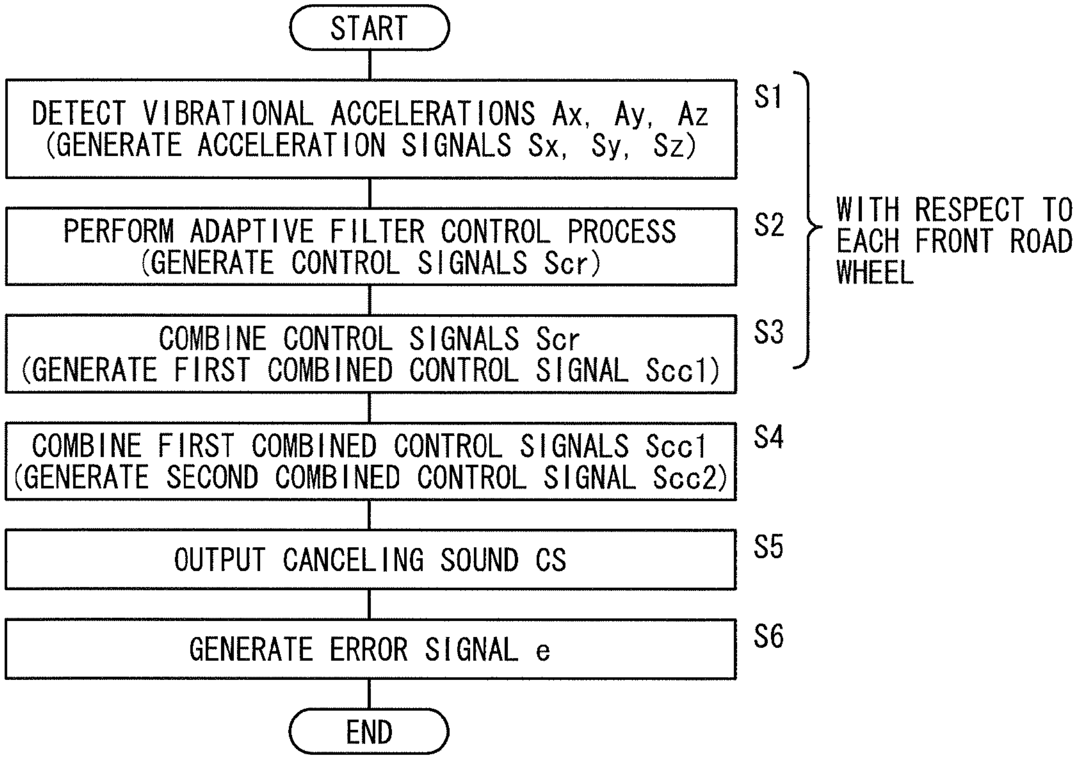
FIG. 8 is a flowchart of an operation sequence of the active vibration noise control apparatus for generating canceling sounds.

A processing sequence for generating canceling sounds CS according to the present embodiment will be described below. FIG. 8 is a flowchart of an operation sequence of the active vibration noise control apparatus 12 for generating a canceling sound CS.

In step S1 shown in FIG. 8, the acceleration sensors 60*x*, 60*y*, 60*z* of each of the acceleration sensor units 16 detect a vibrational acceleration Ax along the X-axis direction, a vibrational acceleration Ay along the Y-axis direction, and a vibrational acceleration Az along the Z-axis direction, and generate acceleration signals Sx, Sy, Sz (reference signals Sb), which are indicative of the vibrational accelerations Ax, Ay, Az, respectively.

In step S2, the control signal generators 62 generate respective control signals Scr by performing an adaptive filter control process on the acceleration signals Sx, Sy, Sz, which have been converted into digital signals by the analog-to-digital converters (not shown), the vehicle speed V from the vehicle speed sensor 18, and the error signal e from the microphone 22. As described above, each of the control signals Scr represents the sum of the front road wheel control signal Scr1 and the rear road wheel control signal Scr2.

In step S3, the first adder 64 combines the control signals Scr output from the respective control signal generators 62 into a first combined control signal Scc1.

The ANC apparatus 12 performs the above processing sequence of steps S1 through S3 for each of the acceleration sensor units 16 on the front road wheels 24*a*.

In step S4, the second adder 66 combines the first combined control signals Scc1, which are received from respective first adders 64 of the control signal generating units 68, into a second combined control signal Scc2.

In step S5, the speaker 20 outputs a canceling sound CS based on the second combined control signal Scc2. The second combined control signal Scc2 output from the second adder 66 is converted into an analog signal by a digital-to-analog converter (not shown), and is adjusted in amplitude by an amplifier (not shown) before being applied to the speaker 20.

In step S6, the microphone 22 detects a difference between the composite noise NZc including the road noise NZr and the canceling sound CS as residual noise, and outputs an error signal e representative of residual noise to the ANC apparatus 12. The error signal e is subsequently used in the adaptive filter control process, which is carried out by the ANC apparatus 12.

The ANC apparatus 12 repeats the processing sequence of steps S1 through S6 in each calculating period Pc.

3. Advantages of the Embodiment

According to the present embodiment, as described above, it is possible to predict a rear road wheel noise canceling sound CSr nicely from reference signals Sb (front road wheel reference signals), in view of different characteristics of the front road wheel suspensions 14*a* and the rear road wheel suspensions 14*b*.

B. Applications of the Invention

The present invention is not limited to the above embodiment, but may employ various alternative arrangements based on the contents of the present description. For example, the present invention may employ the arrangements described below.

1. Acceleration Sensor Units 16

In the above embodiment, the acceleration sensor units 16 are associated respectively with the front road wheels 24*a*. However, an acceleration sensor unit 16 may be associated with only one of the front road wheels 24*a*. Further, in the above embodiment, each of the acceleration sensor units 16 detects vibrational accelerations Ax, Ay, Az along directions of three axes, i.e., an X-axis direction, a Y-axis direction, and a Z-axis direction. However, the acceleration sensor units 16 may detect vibrational accelerations along directions of one axis, two axes, or four or more axes.

In the above embodiment, vibrational accelerations Ax, Ay, Az are detected directly by the acceleration sensors 60*x*, 60*y*, 60*z*. However, a displacement [mm] of the knuckle 30 may be detected by a displacement sensor, whereby vibrational accelerations Ax, Ay, Az may then be calculated from the detected displacement. Alternatively, vibrational accelerations Ax, Ay, Az may be calculated from a value detected by a load sensor, which is coupled to the knuckle 30. Further alternatively, microphones may be disposed near the front road wheels 24*a*, and vibration noise may be detected by the microphones, such that signals representative of the detected vibration noise may be used instead of the acceleration signals Sx, Sy, Sz.

In the above embodiment, the acceleration sensor units 16 are mounted on respective knuckles 30. However, the acceleration sensor units 16 may be mounted on other parts apart from the respective knuckles 30.

2. Process for Estimating Rear Road Wheel Noise Canceling Sound CSr

(1) First Modification

In the above embodiment, the second delayed reference signal Sbd2 is used as a reference signal, which is applied to the adaptive filter processor 70*b* for the rear road wheel 24*b*. The second delayed reference signal Sbd2 is generated by the corrective filter 76 based on the first delayed reference signal Sbd1 (rear road wheel reference signal), and the first delayed reference signal Sbd1 is generated by the delay setting section 72 based on the reference signal Sb (front road wheel reference signal). The delay amount n used in the delay setting section 72 is calculated by the amount-of-delay calculator 74. As described above, the delay amount n used in the delay setting section 72 can be established based on the vehicle speed V, and the transfer function F1 used in the corrective filter 76 is of a fixed value. Therefore, the functions of the delay setting section 72, the amount-of-delay calculator 74, and the corrective filter 76 can be integrated into one component.

Figure 9:
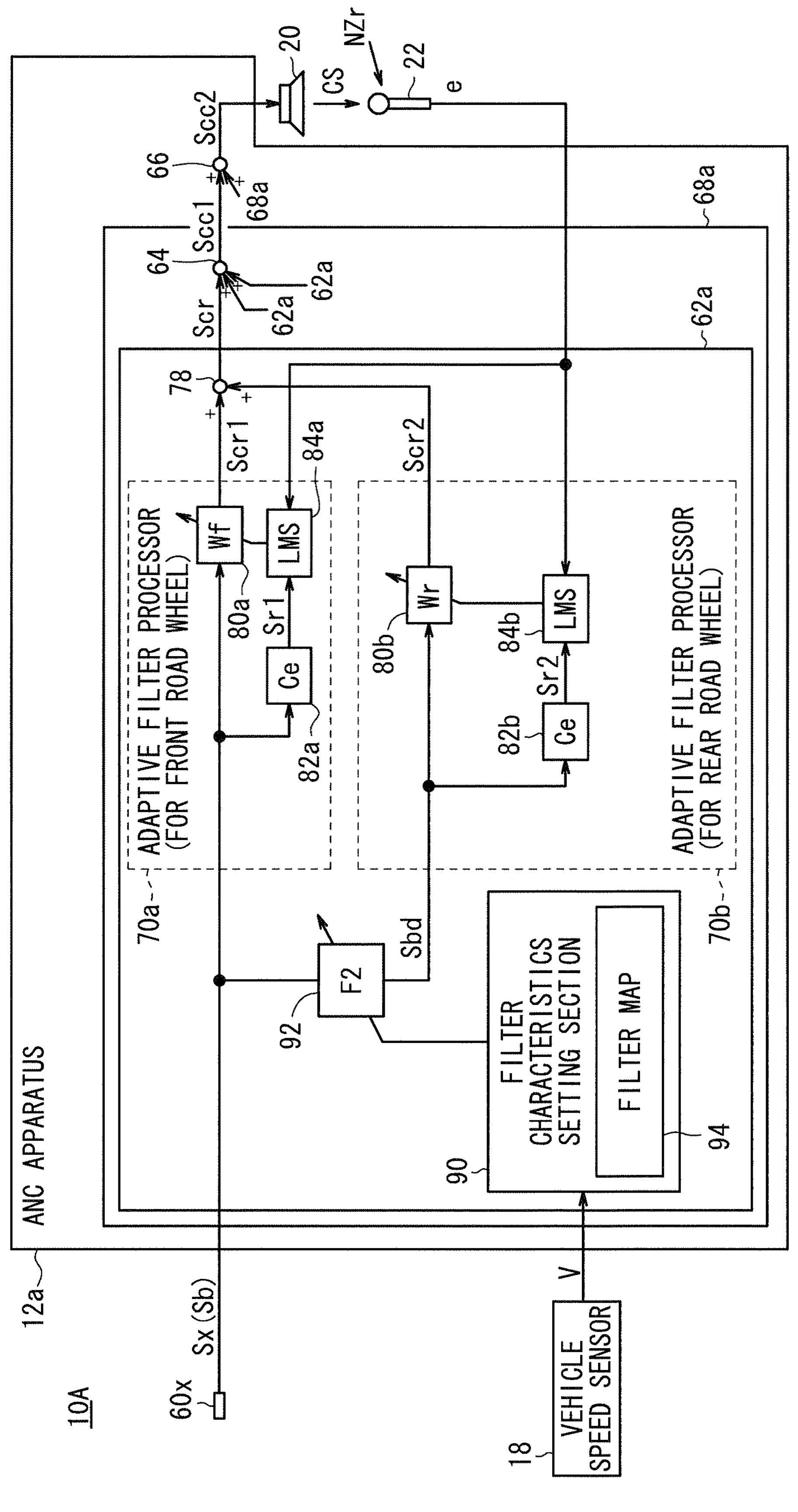
FIG. 9 is a functional block diagram of a control signal generator according to a first modification.

FIG. 9 is a functional block diagram of a control signal generator 62*a* of an active vibration noise control apparatus 12*a* (hereinafter referred to as "ANC apparatus 12*a*") for a motor vehicle 10A according to a first modification. The control signal generator 62*a* shown in FIG. 9 is associated with the acceleration sensor 60*x*. Other control signal generators 62*a*, which are associated with the acceleration sensors 60*y*, 60*z*, are identical in configuration to the control signal generator 62*a* shown in FIG. 9. For illustrative purposes, the control signal generators 62*a* and the first adder 64, which are associated with each of the acceleration sensor units 16, will be referred to collectively as a control signal generating unit 68*a*.

In the ANC apparatus 12 shown in FIG. 5, the second delayed reference signal Sbd2 is generated using the amount-of-delay calculator 74 and the corrective filter 76. In the ANC apparatus 12*a* shown in FIG. 9, a delayed reference signal Sbd is generated using a filter characteristics setting section (delay time calculating unit, rear road wheel reference signal outputting unit) 90 and a corrective filter 92. The delayed reference signal Sbd corresponds to the second delayed reference signal Sbd2 according to the above-described embodiment.

The filter characteristics setting section 90 has a filter map 94 defining a relationship between vehicle speed V from the vehicle speed sensor 18 and transfer functions F2 used by the corrective filter 92. The relationship between the vehicle speed V and the transfer functions F2 in the filter map 94 is reflected in the processing operations carried out by the delay setting section 72, the amount-of-delay calculator 74, and the corrective filter 76 according to the above embodiment. More specifically, the transfer functions F2 are set to values, which reflect both the delay amount n determined from the wheelbase Lwb, the vehicle speed V, and the calculating period Pc, as well as the transfer function F1 based on the different characteristics of the front road wheel suspensions 14*a* and the rear road wheel suspensions 14*b*.

The corrective filter 92, which comprises an FIR filter or an IIR filter, for example, processes the reference signal Sb depending on a transfer function F2, which is set by the filter characteristics setting section 90, and the corrective filter 92 outputs a delayed reference signal Sbd.

The ANC apparatus 12*a* according to the first modification offers the same advantages as the ANC apparatus 12 according to the above embodiment.

(2) Second Modification

In the above embodiment, the second delayed reference signal Sbd2 is calculated based on the front road wheel reference signal (reference signal Sb) and the vehicle speed V. In the first modification, the delayed reference signal Sbd is calculated based on the front road wheel reference signal (reference signal Sb) and the vehicle speed V. The reference signal, which is applied to the adaptive filter processor 70*b* for the rear road wheel 24*b*, may also be calculated in view of other factors.

Figure 10:
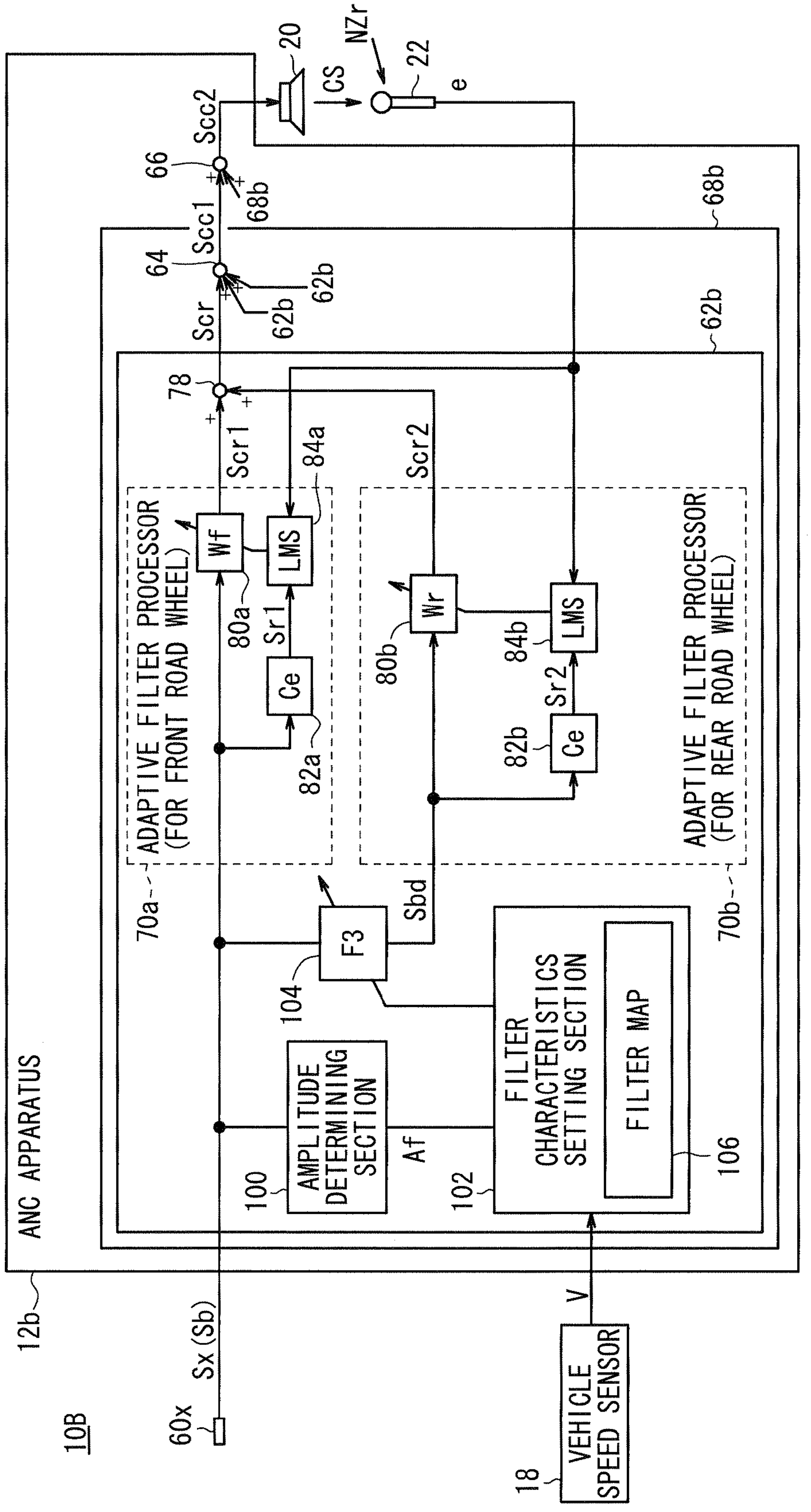
FIG. 10 is a functional block diagram of a control signal generator according to a second modification.

FIG. 10 is a functional block diagram of a control signal generator 62*b* of an active vibration noise control apparatus 12*b* (hereinafter referred to as "ANC apparatus 12*b*") for a motor vehicle 10B according to a second modification. The control signal generator 62*b* shown in FIG. 10 is associated with the acceleration sensor 60*x*. Other control signal generators 62*b*, which are associated with the acceleration sensors 60*y*, 60*z*, are identical in configuration to the control signal generator 62*b* shown in FIG. 10. For illustrative purposes, the control signal generators 62*b* and the first adder 64, which are associated with each of the acceleration sensor units 16, will be referred to collectively as a control signal generating unit 68*b*.

In the ANC apparatus 12*a* shown in FIG. 9, the delayed reference signal Sbd is generated using the filter characteristics setting section 90 and the corrective filter 92, whereas in the ANC apparatus 12*b* shown in FIG. 10, a delayed reference signal Sbd is generated using an amplitude determining section 100, a filter characteristics setting section (delay time calculating unit, rear road wheel reference signal outputting unit) 102, and a corrective filter 104.

The amplitude determining section 100 determines an amplitude Af of the front road wheel reference signal (reference signal Sb), and outputs the determined amplitude Af to the filter characteristics setting section 102.

The filter characteristics setting section 102 has a filter map 106 defining a relationship between vehicle speed V from the vehicle speed sensor 18 and transfer functions F3 used by the corrective filter 104 with respect to each amplitude Af. The relationship between vehicle speed V and transfer functions F3 in the filter map 106 is reflected in the processing operations carried out by the delay setting section 72, the amount-of-delay calculator 74, and the corrective filter 76 according to the above embodiment with respect to each amplitude Af. More specifically, the transfer functions F3 are set to values that reflect both the delay amount n determined from the wheelbase Lwb, the vehicle speed V, and the calculating period Pc, as well as the transfer function F1 based on different characteristics of the front road wheel suspensions 14*a* and the rear road wheel suspensions 14*b* with respect to each amplitude Af.

The corrective filter 104, which comprises an FIR filter or an IIR filter, for example, processes the reference signal Sb depending on a transfer function F3, which is set by the filter characteristics setting section 102, and the corrective filter 104 outputs a delayed reference signal Sbd.

The ANC apparatus 12*b* according to the second modification offers the same advantages as the ANC apparatus 12 according to the above embodiment.

According to the second modification, furthermore, the transfer functions F3 are changed for the corrective filter 104 depending on the determined amplitude Af of the reference signal Sb (front road wheel reference signal). When the amplitude Af is changed, spring characteristics of the front road wheel suspensions 14*a* and the rear road wheel suspensions 14*b* also are changed. According to the second modification, since the transfer functions F3 are changed for the corrective filter 104 depending on the determined amplitude Af of the reference signal Sb, it is possible to output the rear road wheel noise canceling sound CSr depending on respective spring characteristics of the front road wheel suspensions 14*a* and the rear road wheel suspensions 14*b*, thereby increasing the accuracy with which the rear road wheel noise canceling sound CSr is predicted.

(3) Transfer Functions F1, F2, F3 of the Corrective Filters 76, 92, 104

In the above embodiment, the first modification, and the second modification, the transfer functions F1, F2, F3 are used to adjust the gain and phase of the reference signals Sb. However, the reference signals Sb may be adjusted in other ways. For example, only one of the gain and phase of the reference signals Sb may be adjusted.

3. Other Features

In the above embodiment, the amount-of-delay calculator 74 is included in each of the control signal generators 62. However, the ANC apparatus 12 may include a single amount-of-delay calculator 74, whereby the single amount-of-delay calculator 74 is capable of establishing delay amounts n for the respective control signal generators 62.

Although certain preferred embodiments of the present invention have been shown and described in detail, it should be understood that various changes and modifications may be made to the embodiments without departing from the scope of the invention as set forth in the appended claims.

What is claimed is:

1. An active vibration noise control apparatus comprising:

a front road wheel vibration detecting unit configured to detect front road wheel vibrations based on an input applied from a road surface to a front road wheel of a vehicle, and output a front road wheel reference signal representative of the detected front road wheel vibrations;

a vehicle speed detecting unit configured to detect a vehicle speed of the vehicle;

a delay time calculating unit configured to determine a delay time, which is representative of a difference between respective times when the front road wheel of the vehicle and a rear road wheel of the vehicle pass through a point, based on the vehicle speed;

a rear road wheel reference signal outputting unit configured to output a rear road wheel reference signal, which is representative of predicted rear road wheel vibrations, comprising the front road wheel vibrations delayed by the delay time; and a canceling sound outputting unit configured to output a front road wheel noise canceling sound, which cancels out front road wheel vibration noise caused by the front road wheel vibrations at a noise silencing position, based on the front road wheel reference signal, and output a rear road wheel noise canceling sound, which cancels out rear road wheel vibration noise caused by the predicted rear road wheel vibrations at the noise silencing position, based on the rear road wheel reference signal, and a corrective filter configured to reflect a characteristic difference between front road wheel suspensions and rear road wheel suspensions of the vehicle in the rear road wheel reference signal by correcting the rear road wheel reference signal prior to being output by the corrective filter, based on the characteristic difference.

2. The active vibration noise control apparatus according to claim 1, wherein the rear road wheel reference signal outputting unit changes characteristics of the corrective filter depending on an amplitude of the front road wheel reference signal.

3. The active vibration noise control apparatus according to claim 1, wherein a transfer function in the corrective filter is applied to the rear road wheel reference signal and is established for correcting a deviation between amplitudes of acceleration signals that were previously measured on the front road wheel suspensions and the rear road wheel suspensions of the vehicle.

4. The active vibration noise control apparatus of claim 1, wherein the noise canceling sounds output by the canceling sound outputting unit are substantially in opposite phase with the vibration noises.

5. An active vibration noise control apparatus comprising:

a front road wheel vibration detecting unit configured to detect front road wheel vibrations based on an input applied from a road surface to a front road wheel of a vehicle, and output a front road wheel reference signal representative of the detected front road wheel vibrations;

a vehicle speed detecting unit configured to detect a vehicle speed of the vehicle;

a delay time calculating unit configured to determine a delay time, which is representative of a difference between respective times when the front road wheel of the vehicle and a rear road wheel of the vehicle pass through a point, based on the vehicle speed;

a rear road wheel reference signal outputting unit configured to output a rear road wheel reference signal, which is representative of predicted rear road wheel vibrations, comprising the front road wheel vibrations delayed by the delay time; and a canceling sound outputting unit configured to output a front road wheel noise canceling sound, which cancels out front road wheel vibration noise caused by the front road wheel vibrations at a noise silencing position, based on the front road wheel reference signal, and output a rear road wheel noise canceling sound, which cancels out rear road wheel vibration noise caused by the predicted rear road wheel vibrations at the noise silencing position, based on the rear road wheel reference signal, and a corrective filter configured to reflect a characteristic difference between front road wheel suspensions and rear road wheel suspensions of the vehicle in the rear road wheel reference signal by correcting the rear road wheel reference signal prior to being output by the corrective filter, based on the characteristic difference, wherein the corrective filter is configured to output a delayed reference signal, which is delayed by an amount calculated by a delay calculator.

6. The active vibration noise control apparatus of claim 5, wherein the noise canceling sounds output by the canceling sound outputting unit are substantially in opposite phase with the vibration noises.

7. An active vibration noise control apparatus comprising:

a front road wheel vibration detecting unit configured to detect front road wheel vibrations based on an input applied from a road surface to a front road wheel of a vehicle, and output a front road wheel reference signal representative of the detected front road wheel vibrations;

a vehicle speed detecting unit configured to detect a vehicle speed of the vehicle;

a delay time calculating unit configured to determine a delay time, which is representative of a difference between respective times when the front road wheel of the vehicle and a rear road wheel of the vehicle pass through a point, based on the vehicle speed;

a first rear road wheel reference signal outputting unit configured to output a first rear road wheel reference signal, which is representative of predicted rear road wheel vibrations, comprising the front road wheel vibrations delayed by the delay time; and a canceling sound outputting unit configured to output a front road wheel noise canceling sound, which cancels out front road wheel vibration noise caused by the front road wheel vibrations at a noise silencing position, based on the front road wheel reference signal, and output a rear road wheel noise canceling sound, which cancels out rear road wheel vibration noise caused by the predicted rear road wheel vibrations at the noise silencing position, based on the first rear mad wheel reference signal;

a corrective filter configured to reflect a characteristic difference between front road wheel suspensions and rear road wheel suspensions of the vehicle in the first rear road wheel reference signal by correcting the first rear road wheel reference signal prior to being output by the corrective filter, based on the characteristic difference; and an amplitude determining section configured to determine an amplitude of the front road wheel reference signal, wherein:

the first rear road wheel reference signal outputting unit changes characteristics of the corrective filter depending on the amplitude of the front road wheel reference signal determined by the amplitude determining section, a transfer function in the corrective filter is established in a state where a rear road wheel detecting unit configured to detect rear road wheel vibrations based on an input applied from a road surface to the rear road wheel and the front road wheel vibration detecting unit are installed on the vehicle, for correcting a deviation between an amplitude of the front road wheel reference signal output from the front road wheel vibration detecting unit and an amplitude of a second rear road wheel reference signal output from the rear road wheel vibration detecting unit as representative of the detected rear road wheel vibrations, and for the calculation of the deviation, the amplitude of the front road wheel reference signal and the amplitude of the second rear road wheel reference signal are compared at each frequency, and for the calculation of the deviation, the amplitude of the second rear road wheel reference signal is delayed by the delay time from a time at which the amplitude of the front road wheel reference signal was acquired.

8. The active vibration noise control apparatus of claim 7, wherein the noise canceling sounds output by the canceling sound outputting unit are substantially in opposite phase with the vibration noises.

* * * * *